United States Patent [19]

Zimmerman et al.

[11] 4,264,577
[45] Apr. 28, 1981

[54] CONTRACEPTIVE METHODS AND COMPOSITIONS

[75] Inventors: Ronald E. Zimmerman, Danville; Philip J. Burck, Indianapolis; C. David Jones, Indianapolis; Arvind L. Thakkar, Indianapolis, all of Ind.

[73] Assignee: Eli Lilly and Company, Indianapolis, Ind.

[21] Appl. No.: 138,393

[22] Filed: Apr. 8, 1980

Related U.S. Application Data

[63] Continuation-in-part of Ser. No. 63,507, Aug. 3, 1979, abandoned, Continuation of Ser. No. 973,251, Dec. 26, 1978, abandoned.

[51] Int. Cl.³ .................. A61K 9/02; A61K 9/22; A61K 9/26; A61K 9/70
[52] U.S. Cl. ..................... 424/22; 128/260; 424/19; 424/28
[58] Field of Search ..................... 424/19–22, 424/28

[56] References Cited

U.S. PATENT DOCUMENTS

| 3,279,996 | 10/1966 | Long et al. | 424/32 |
|---|---|---|---|
| 3,545,439 | 12/1970 | Duncan | 128/260 |
| 3,888,975 | 6/1975 | Ramwell | 424/15 |
| 3,903,880 | 9/1975 | Higuchi et al. | 128/130 |
| 3,920,805 | 11/1975 | Roseman | 424/15 |
| 4,012,496 | 3/1977 | Schopflin | 424/15 |
| 4,012,497 | 3/1977 | Schopflin | 424/22 |
| 4,014,987 | 3/1977 | Heller et al. | 424/15 |
| 4,016,251 | 4/1977 | Higuchi et al. | 424/15 |
| 4,034,749 | 7/1977 | Von Kesserv et al. | 128/130 |
| 4,053,580 | 10/1977 | Chien et al. | 424/15 |
| 4,067,961 | 1/1978 | Laughlin | 424/15 |

OTHER PUBLICATIONS

Mathews, M. B., J.A.C.S. 76:2948–2952 (1954) Testicular Hyaluronidase in Relation to Micelle Formation by Inactivating Agents.

Zanefield, L. Sperm Enzyme Inibitors as Antifertility Agents Chap. 56: 570–582 of Human Semen and Fertility Regulation in Men, E. Hafez Ed. C. V. Mosby Co., St. Louis Mo. (1976).

"Barrier Methods" Population Reports Series H No. 5 Sep. 1979 H–76 to H–118.

Primary Examiner—Shep K. Rose
Attorney, Agent, or Firm—James L. Rowe; Arthur R. Whale

[57] ABSTRACT

Introduction of a compound of the formula:

$$R-OSO_3-M$$

wherein R is:

(a) $C_{11}$–$C_{30}$ straight chain alkyl or alkenyl;
(b) $C_{10}$–$C_{30}$ branched chain alkyl or alkenyl, the α-carbon of which is not branched; or
(c) $C_{13}$–$C_{30}$ branched chain alkyl or alkenyl, the α-carbon of which is branched, and M is a pharmaceutically acceptable non-toxic cation; into the uterine lumen or vaginal cavity prevents conception. Sodium n-tetradecyl sulfate is preferred.

8 Claims, No Drawings

CONTRACEPTIVE METHODS AND COMPOSITIONS

This is a continuation-in-part of application Ser. No. 063,507, filed Aug. 3, 1979, now abandoned which is a continuation of application Ser. No. 973,251, filed Dec. 26, 1978, now abandoned.

This invention relates to improved methods and compositions useful in human and veterinary medicine for the control of fertility.

Contraceptive methods involving the administration of chemical substances are widely practiced among women who desire to limit pregnancies. Such methods control fertility through various biological mechanisms. Among the presently used chemical methods of fertility control, the most important are those which act by means of the following: (a) suppression of ovulation through inhibition of gonadotropin release; (b) alteration of the female reproductive tract to prevent migration of sperm to the site of fertilization or, if fertilization occurs, to block implantation of the zygote (nidation); or (c) spermicidal action.

The oral contraceptives are the most prominent chemical contraceptive agents. These agents are of two types: (a) an estrogen combined with a progestin, and (b) a progestin alone. The contraceptives of the combined type act primarily by suppressing ovulation by negative feedback to prevent gonadotropin (LH and FSH) release by the hypothalamus, but alterations in the reproductive tract may also contribute to the antifertility effect. Such alterations include changes in the cervical mucus (which increase the difficulty of sperm migration) and in the endometrium (which decrease the likelihood of nidation). The action of a progestin alone in a very low oral dose (the "mini-pill") appears to involve primarily alterations in the female reproductive tract, but ovulation suppression may also occur. Although the oral contraceptives are highly effective, their use is associated with unpleasant side effects (such as nausea, depression, weight-gain, and headache) and an increased long-time risk of severe disease (such as thromboembolism, stroke, myocardial infarction, hepatic adenoma, gall bladder disease, and hypertension). Bleeding irregularities (such as break-through bleeding, spotting, and amenorrhea) are also frequent. A progestin, when administered alone, causes an increased incidence of changes in menstrual patterns, especially a marked increase in the amount and duration of menstrual bleeding.

Besides the oral route of administration a progestin alone may be administered systemically by various sustained-release dosage forms which include: (a) depo injection (IM) of an insoluble progestin (e.g. medroxy progesterone acetate), (b) a subdermal implant, or (c) an intravaginal insert. With these methods of administration, the progestin is absorbed into the body continuously at a very low daily dose, and the systemic effects are similar to those produced by oral administration of a progestin. However, as with the oral progestins, the sustained release methods may cause serious menstrual flow irregularities.

A recent method of contraception involves the sustained release of progesterone locally within the uterine lumen. In this method the progesterone is incorporated into a chamber within a flexible intrauterine device (IUD) formed from a polymer which is capable of releasing progesterone continuously into the uterine fluids at a slow rate over a prolonged period of time. The progesterone acts primarily locally to produce progestational alterations in the cervical mucus and endometrium. However, the antifertility action may also be caused by the reaction of the endometrium to the device itself ("IUD effect") or by systemic absorption of progesterone through the uterine membrane. Again, as with other progestin-only therapies, there is an increased incidence of menstrual flow irregularities. Another disadvantage of this method, is the increased risk of ectopic pregnancy.

Another recent development is the flexible IUD bearing metallic copper. The contraceptive action of this device results from the combined effects of the copper (which very slowly dissolves in the uterine fluids), which acts on the blastocyst and on the cervical mucus or endometrium, and of the IUD itself, which causes a foreign body reaction in the endometrium.

Other chemical methods of contraception include the post coital administration of estrogens (e.g. diethylstilbestrol or ethynylestradiol) to prevent nidation or of prostaglandins which act as abortifacients. Both of these methods, at present, are limited to emergency situations. Still in the very early stages of development are immunological methods (vaccination) and methods involving the direct control of LHRH secretion from the pituitary by LHRH agonists or antagonists.

Another group of chemical contraceptive agents are the local spermatocides, such as nonoxynol or octoxynol, which are placed into the vagina immediately prior to coitus in the form of creams, foams, jellies, or suppositories. The spermicidal action takes place either in the vagina or elsewhere in the reproductive tract. For the latter to occur, the spermicidal agent is either adsorbed on sperm membranes or is transported into the uterus under the influence of uterine contractions. The spermicidal methods are less reliable in preventing pregnancy and are inconvenient to use.

The intrauterine device (IUD) is the most common alternative to the oral contraceptives. The anti-fertility effect of the IUD is not caused by chemical activity. Instead the material forming the IUD induces a foreign body reaction (irritation) in the contiguous endometrium which appears to interfere in some way with nidation. The use of the IUD is complicated, however, by serious problems including the possibility of intrauterine perforation, pelvic inflammation, discomfort, or aggravated menstrual periods.

From the foregoing, it is evident that the presently available methods of contraception are inadequate for various reasons because they: (a) may produce unpleasant side effects or increase the risk of serious disease, (b) may be unreliable, or (c) may be inconvenient and intrude on sexual enjoyment. Although many women practice contraception in spite of these inadequacies, a need exists in medicine for improved methods which combine effectiveness with increased safety and convenience. Such improvements are afforded by the present invention.

It has now been surprisingly found that a class of alkyl or alkenyl sulfate salts (to be more fully described below) will effectively prevent fertilization when introduced in very small amounts in the female reproductive tract prior to coitus. The alkyl or alkenyl sulfate salts, being non-steroidal, do not produce hormonal effects either locally or systemically, and, hence, they offer significant advantages over the oral contraceptive steroids and the sustained release progestin compositions heretofore used. The antifertility effect of the alkyl or alkenyl sulfate salts can be demonstrated in female rabbits using standard pharmacological test procedures whereby the test compound is introduced locally within the reproductive tract of the animal, the animal is then bred to a fertile buck, and the genital system of the animal is then examined to determine the number of embryos.

The alkyl or alkenyl sulfate salts can be delivered satisfactorily within the female reproductive tract by slow release from silicone rubber compositions. Silicone rubber is known to be a useful vehicle for the sustained delivery of certain medicaments. Administration of an alkyl or alkenyl sulfate salt in the female reproductive tract by means of a sustained release silicone rubber composition will provide a more convenient and acceptable method of contraception than has heretofore been employed in the prior art.

The invention sought to be patented in its method of use aspects constitutes:

1. A method of contraception in a female mammal which comprises continuously introducing within the uterine lumen of said female, over a prolonged period of time at a controlled rate, an effective amount of a compound of the formula:

R—OSO₃—M wherein R is:
(a) $C_{11}$-$C_{30}$ straight chain alkyl or alkenyl;
(b) $C_{10}$-$C_{30}$ branched chain alkyl or alkenyl, the α-carbon of which is not branched; or
(c) $C_{13}$-$C_{30}$ branched chain alkyl or alkenyl, the α-carbon of which is branched;
and M is a pharmaceutically acceptable non-toxic cation.

2. A method of contraception in a female mammal which comprises continuously introducing within the vaginal cavity of said female, over a prolonged period of time at a controlled rate, an effective amount of a compound of the formula:

R—OSO₃—M wherein R is:
(a) $C_{11}$-$C_{30}$ straight chain alkyl or alkenyl;
(b) $C_{10}$-$C_{30}$ branched chain alkyl or alkenyl, the α-carbon of which is not branched; or
(c) $C_{13}$-$C_{30}$ branched chain alkyl or alkenyl, the α-carbon of which is branched;
and M is a pharmaceutically acceptable non-toxic cation; whereby the compound is transported into the uterine fluids with sperm during or after coitus; or 3. A method of contraception in a female mammal which comprises introducing into the vaginal cavity immediately before coitus an effective amount of a compound of the formula:

R—OSO₃—M
wherein R is:

(a) $C_{11}$-$C_{30}$ straight chain alkyl or alkenyl;
(b) $C_{10}$-$C_{30}$ branched chain alkyl or alkenyl, the α-carbon of which is not branched; or
(c) $C_{13}$-$C_{30}$ branched chain alkyl or alkenyl, the α-carbon of which is branched;
and M is a pharmaceutically acceptable non-toxic cation; whereby the compound is transported into the uterine fluids with sperm during or after coitus.

In its composition aspects, the present invention comtemplates:

1. A contraceptive composition suitable for insertion and comfortable retention in the uterine lumen which comprises: (a) about 1 to about 40 percent by weight of a compound of the formula:

R—OSO₃—M wherein R is:
(a) $C_{11}$-$C_{30}$ straight chain alkyl or alkenyl;
(b) $C_{10}$-$C_{30}$ branched chain alkyl or alkenyl, the α-carbon of which is not branched; or
(c) $C_{13}$-$C_{30}$ branched chain alkyl or alkenyl, the α-carbon of which is branched;
and M is a pharmaceutically acceptable non-toxic cation; and (b) about 60 to about 99 percent by weight of a biocompatible, bioinsoluble, flexible silicone rubber carrier matrix, said matrix being capable of continuously releasing said compound into the uterine fluids at a controlled rate over a prolonged period of time; or 2. A contraceptive composition suitable for insertion and comfortable retention in the vaginal cavity which comprises: (a) about 1 to about 40 percent by weight of compound of the formula:

R—OSO₃—M wherein R is:
(a) $C_{11}$-$C_{30}$ straight chain alkyl or alkenyl;
(b) $C_{10}$-$C_{30}$ branched chain alkyl or alkenyl, the α-carbon of which is not branched; or
(c) $C_{13}$-$C_{30}$ branched chain alkyl or alkenyl, the α-carbon of which is branched;
and M is a pharmaceutically acceptable non-toxic cation; and (b) about 60 to about 99 percent by weight of a biocompatible, bioinsoluble, flexible silicone rubber carrier matrix, said matrix being capable of continuously releasing said compound into the vaginal fluids at a controlled rate over a prolonged period of time; or 3. A contraceptive foam, jelly, cream, suppository, or sponge composition suitable for comforatable insertion into the vaginal cavity which comprises: (a) an effective amount of compound of the formula:

R—OSO₃—M wherein R is:
(a) $C_{11}$-$C_{30}$ straight chain alkyl or alkenyl;
(b) $C_{10}$-$C_{30}$ branched chain alkyl or alkenyl, the α-carbon of which is not branched; or
(c) $C_{13}$-$C_{30}$ branched chain alkyl or alkenyl, the α-carbon of which is branched;
and M is a pharmaceutically acceptable non-toxic cation; and (b) a pharmaceutically acceptable, non-toxic vaginal excipient.

As employed herein and in the claims, the term "α-carbon" denotes the carbon atom of the alkyl or alkenyl group (R) which is bonded to the oxygen atom of the sulfate function (—O—SO₃—). When the α-carbon atom is not branched, it will be understood that the α-carbon atom is bonded to only one carbon atom of the alkyl or alkenyl group (R). When the α-carbon is branched, the α-carbon is bonded to at least two carbon atoms of the alkenyl or alkenyl group (R). It will be also understood that when the α-carbon is branched, further branching may occur at other carbon atoms of the alkyl or alkenyl group (R). As employed herein and in the claims, the term "alkenyl" means an unsaturated branched chain or straight chain univalent hydrocarbon radical which may contain one or two double bonds. The double bonds may be oriented in either the cis or trans configuration. As will be apparent to one skilled in the art, the double bond cannot be located in the alkenyl chain at either the α-carbon or β-carbon relative to the sulfate function. Moreover, when the alkenyl group contains two double bonds, the double bonds must not be adjacent to each other.

Illustrative alkyl groups (R) are as follows:

A. A straight chain alkyl group of the formula:

$$CH_3(CH_2)_n-$$

wherein n is an integer from 10 to 29 (preferably 10 to 20); for example:
n-undecyl, n-dodecyl, n-tridecyl, n-tetradecyl, n-pentadecyl, n-hexadecyl, n-heptadecyl, n-octadecyl, n-nonadecyl, n-eicosyl, and the like.

B. An α-branched chain alkyl group of the formula:

$$\underset{CH_3(CH_2)_oCH-}{\overset{(CH_2)_pCH_3}{|}}$$

wherein o and p are, independently, each an integer from 0 to 27, provided that o+p must be no less than 7 and no greater than 27; for example:

| | |
|---|---|
| $CH_3(CH_2)_{11}\overset{\overset{CH_3}{\|}}{CH}-$ | 2-tetradecyl |
| $CH_3(CH_2)_9\overset{\overset{(CH_2)_2CH_3}{\|}}{CH}-$ | 4-tetradecyl |
| $CH_3(CH_2)_7\overset{\overset{(CH_2)_4CH_3}{\|}}{CH}-$ | 6-tetradecyl |
| $CH_3(CH_2)_6\overset{\overset{(CH_2)_5CH_3}{\|}}{CH}-$ | 7-tetradecyl |
| $CH_3(CH_2)_8\overset{\overset{(CH_2)_5CH_3}{\|}}{CH}-$ | 7-hexadecyl |
| $CH_3(CH_2)_7\overset{\overset{(CH_2)_6CH_3}{\|}}{CH}-$ | 8-hexadecyl |
| $CH_3(CH_2)_8\overset{\overset{(CH_2)_7CH_3}{\|}}{CH}-$ | 9-octadecyl. |

C. A branched chain alkyl group not branched at the α-carbon, of the formula:

$$CH_3(CH_2)_q\overset{\overset{CH_3}{\|}}{CH}(CH_2)_rCH_2- \quad (a)$$

wherein r and q are, independently, each an integer from 0 to 26, provided that r+q must be no less than 6 and no greater than 26; for example:

$$CH_3\overset{\overset{CH_3}{\|}}{CH}(CH_2)_{11}- \quad 12\text{-methyltridecyl;} \quad (b)$$

$$CH_3\overset{\overset{CH_3}{\|}}{CH}(CH_2)_a\overset{\overset{CH_3}{\|}}{CH}(CH_2)_b-$$

wherein a and b are, independently, each an integer from 1 to 24, provided that a+b must be no less than 5 and no greater than 25; for example:

$$CH_3\overset{\overset{CH_3}{\|}}{CH}(CH_2)_3\overset{\overset{CH_3}{\|}}{CH}CH_2CH_2 \quad \text{tetrahydrogeranyl;} \quad (c)$$

$$CH_3\overset{\overset{CH_3}{\|}}{CH}(CH_2)_c\overset{\overset{CH_3}{\|}}{CH}(CH_2)_d\overset{\overset{CH_3}{\|}}{CH}(CH_2)_e-$$

wherein c, d, and e are, independently, each an integer from 1 to 21, provided that c+d+e must be no greater than 23; for example:

$$CH_3\overset{\overset{CH_3}{\|}}{CH}(CH_2)_3\overset{\overset{CH_3}{\|}}{CH}(CH_2)_3\overset{\overset{CH_3}{\|}}{CH}(CH_2)_2 \quad \text{3,7,11-trimethyldodecyl; or} \quad (d)$$

$$CH_3(CH_2)_f\overset{\overset{(CH_2)_gCH_3}{\|}}{CH}CH_2-$$

wherein f and g are, independently, each an integer from 0 to 26, provided that g+f must be no less than 6 and no greater than 26; for example:

$$CH_3(CH_2)_q\overset{\overset{(CH_2)_7CH_3}{\|}}{CH}CH_2- \quad \text{2-octyldodecyl.}$$

Illustrative alkenyl groups (R) are as follows:

A. A monounsaturated straight chain alkenyl group of the formula:

$$CH_3(CH_2)_tCH=CH(CH_2)_sCH_2-$$

wherein t is an integer from 0 to 25 and s is an integer from 1 to 26, provided that t+s must be no less than 7 and no greater than 26; for example:

| | |
|---|---|
| cis $-CH_3(CH_2)_3CH=CH(CH_2)_8-$ | myristoleyl |
| trans $-CH_3(CH_2)_3CH=CH(CH_2)_8-$ | myristeladyl |
| cis $-CH_3(CH_2)_7CH=CH(CH_2)_8-$ | oleyl |
| trans $-CH_3(CH_2)_7CH=CH(CH_2)_8-$ | eladyl |

B. A di-unsaturated straight chain alkenyl group of the formula:

$$CH_3(CH_2)_xCH=CH(CH_2)_yCH=CH-(CH_2)_zCH_2-$$

wherein x is an integer from 0 to 22 and y and z are, independently, each an integer from 1 to 23; provided x+y+z must be no less than 5 and no greater than 24; for example:

$$\text{cis,cis}-CH_3(CH_2)_4CH=CHCH_2CH=CH(CH_2)_8-\text{linoleyl}$$

C. A monounsaturated branched chain alkenyl group of the formula:

$$CH_3\overset{\overset{CH_3}{\|}}{CH}-(CH_2)_wCH=CH-(CH_2)_u-CH_2$$

wherein w is an integer from 0 to 23 and u is an integer from 1 to 24, provided that w+u must be no less than 4 and no greater than 24; for example:

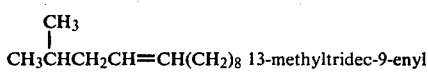
CH$_3$CHCH$_2$CH=CH(CH$_2$)$_8$  13-methyltridec-9-enyl

The cation (M) of the compounds of the formula R—OSO$_3$—M can be any pharmaceutically acceptable, non toxic cation such as sodium, potassium, lithium, calcium, magnesium, copper, aluminum, pyridinium, substituted pyridnium, zinc, ammonium, or substituted ammonium, e.g. diethanolammonium or triethanolammonium. It will be appreciated by those skilled in the art that when the cation (M) has a valency greater than one, more than one alkyl sulfate moiety will be associated with the cation. The C$_{11}$-C$_{20}$ alkyl sulfates are available commercially in the form of the sodium salt. The sodium salts are preferred for the purposes of this invention. The salts can be prepared by methods well known in the art of chemistry.

The alkyl or alkenyl sulfate salts of the formula R—OSO$_3$—M, wherein R and M have the meanings hereinabove defined, are either known compounds, or they can be made from known compounds by known reactions or by modifications thereof which will be obvious to those skilled in the art.

One method for preparing the alkyl or alkenyl sulfates employed in this invention is by treating the appropriate alkanol or alkenol (R—OH) with chlorosulfonic acid in a non-reactive organic solvent (e.g. hexane or tetrahydrofuran). The reaction can be carried out at room temperature or with mild heating (to about 50°), or it can be carried out at low temperatures (to $-25°$ C.) to prevent side reaction with sensitive starting materials. The product is reacted with a suitable base in order to obtain the particular cation salt which is desired.

Another method for preparing the alkyl or alkenyl sulfate salts is by reacting the appropriate alkanol or alkenol with "pyridine-sulfur trioxide complex" in the presence of pyridine and acetic anhydride in a non reactive solvent (e.g. toluene). The reaction is carried out, preferably, at an elevated temperature (e.g. 80° to 150° C.). The product of the reaction forms as the pyridinium salt, but other salts can be formed by treating the pyridinium salt with a suitable base, such as potassium hydroxide, sodium hydroxide, lithium hydroxide, calcium hydroxide, magnesium hydroxide, etc.

The alkyl or alkenyl sulfate salts have surface-active properties, and the sodium salts of dodecyl sulfate (lauryl sulfate), tetradecyl sulfate (myristyl sulfate), and hexadecyl sulfate (cetyl sulfate) are particularly useful surfactants for many applications. Sodium lauryl sulfate, for example, is widely used in topical creams, lotions and other preparations used for pharmaceutical or cosmetic purposes. A mixture of sodium lauryl sulfate and sodium myristyl sulfate is used commercially as a wetting agent, primarily in the paper industry. It is well known that surfactants may denature proteins when present in aqueous solutions in sufficient concentrations because the surface activity may affect peptide conformation. Sodium n-tetradecyl sulfate does not show classical spermicidal activity in standard in vitro tests which measure the ability of the compounds to kill or immobilize sperm.

The alkyl or alkenyl sulfate salts control fertility by inhibiting enzymes which are required during fertilization to allow sperm to penetrate the outer investments of the ovum. An ovum contains three outer investments-the cumulus oophorus, the corona radiata, and the zona pellucida-which are barriers to fertilization. In the male and when first deposited in the female, sperm is incapable of fertilizing an ovum since it lacks the capacity to penetrate the outer investments. Before ferilization can occur, specific hydrolytic enzymes emanating from the sperm must digest each investment so as to form a passage for sperm penetration. The process by which sperm achieve the ability to penetrate the ovum is know as "capacitation". Capacitation involves the labilization of sperm membranes and the release, activation, or exposure of the ovum penetrating enzymes as needed to attack each investment. There is evidence that the activation of the ovum penetrating enzymes may involve the removal of specific inhibitors of the enzymes. The exact biochemical transformations occurring during capacitation are not fully understood, but the enzymes must exert their action either while bound to the sperm membranes or upon release from sperm after the sperm and the ovum make contact in the fallopian tube. For a review of the biochemistry of capacitation and of the inhibition of ovum penetrating enzymes see McRorie et al., Ann. Rev. Biochem., 43, 777 (1974) and E. S. Hafez, Ed., "Human Semen and Fertility Regulation in Men", C. V. Mosby Co., St. Louis, Mo., 1976, pages 201 to 242 and 563 to 582.

It is believed that the alkyl or alkenyl sulfate salts inhibit in vitro the action of hyaluronidase and/or acrosin, the sperm acrosomal enzymes which are known to be responsible in vivo for the penetration of the cumulus oophorus and the zona pellucida, respectfully. Hyaluronidase is a glycosidase which causes degradation of the hyaluronic acid which occurs between the cells of the cumulus oophorus. Acrosin is a proteinase which causes degradation of the glycoproteins of the zona pellucida. Inhibition of each of these enzymes in vivo will lead to interruption of the ovum penetration process thereby effectively preventing fertilization and pregnancy. The inhibition of hyaluronidase (from bull testes) in vitro by C$_{12}$-C$_{14}$ alkyl sulfate sodium salts is described by M. Mathews, J. Am. Chem. Soc., 76, 2948 (1954).

The ability of sodium n-tetradecyl sulfate to prevent digestion of the cumulus oophorus and/or the zona pellucida has been demonstrated in in vitro tests wherein an isolated ovum from a rabbit is observed under a microscope while being incubated in calcium-free Ringer's solution in the presence of testicular hyaluronidase or acrosin with and without sodium n-tetradecyl sulfate being present in the medium. In the absence of sodium n-tetradecyl sulfate, complete removal of the cumulus oophorus and zona pellucida is observed. With sodium n-tetradecyl sulfate present, the cumulus oophorus and zona pellucida remain substantially intact.

In order to prevent pregnancy, an effective, amount of the alkyl or alkenyl sulfate salt must be present at the site of fertilization in the fallopian tube when sperm and the ovum make contact prior to penetration of the ovum. The alkyl or alkenyl sulfate salt can be administered by introduction locally either within the uterine lumen or vaginal cavity. By both modes of administration, the alkyl or alkenyl sulfate salt is carried to the site of fertilization either by adsorbtion onto sperm membranes or by transport through the fluids of the reproductive tract. In uterine fluids, the alkyl or alkenyl sulfate salt reaches the fallopian tube by means of diffusion or active transport. In vaginal fluids, the compound passes to the uterine fluids either adsorbed on sperm membranes or by active transport under the influence of uterine contractions. The preferred method of administration from the stand point of convenience to the female user is to introduce the alkyl or alkenyl sulfate salt continously within the uterus or vagina during the fertile period of the female (i.e. the period three to four days after ovulation when an ovum is present in the fallopian tube). By this method an effective amount of the active compound is present within the reproductive tract each day to prevent fertilization if coitus should occur during the fertile period. Such a method would be independent of the sex act and would avoid the inconvenience of repeated independent dosages.

The continuous administration of the active compound can be accomplished effectively by incorporating it into an organopolysiloxane (silicone rubber) composition and placing said composition into the uterine lumen or vaginal cavity. The active compound is slowly introduced into the uterine or vaginal fluids by release from the silicone rubber at a controlled rate, an effective amount of the compound being present continuously in such fluids. The silicone rubber acts as an insoluble carrier matrix for supporting the active compound while it is being introduced into the uterine or vaginal fluids. Silicone rubber is bioinsoluble and biocompatible (i.e. it is non-toxic, insoluble, and physiologically inert when in contact with body tissues and fluids) and is flexible enough to avoid uterine perforation and to prevent or minimize an IUD effect on the contiguous endometrium. The silicone rubber carrier can be formed in any shape or size suitable for insertion and comfortable retention in the uterine lumen or vaginal cavity. For example, for intrauterine use it can be in the form of a Lippes loop, butterfly, coil, Birnberg bow, or T configuration, or modifications thereof, which configurations are well known in the art to be useful for retention in the uterus. [See, for example, U.S. Pat. Nos. 3,234,938; 3,533,406; 3,935,860; 3,077,879; 3,250,271; and 3,319,625.] For intravaginal use, it can be formed as a flexible ring, similar in configuration to that of the retaining ring of a diaphragm, which is known in the art to be useful for retention in the vagina. [See, U.S. Pat. Nos. 3,545,439 and 3,920,805.]

Organopolysiloxanes are described in U.S. Pat. No. 3,279,996 (Long et al), the disclosure of which is incorporated herein by reference. This patent describes implants for releasing a drug in the tissues of living organisms comprising the drug enclosed in a capsule formed of silicone rubber or the drug dispersed in a prosthesis made from silicone rubber. A number of biocompatible insoluble silicone rubbers are described in the Long et al. patent. A preferred silicone rubber is dimethylpolysiloxane which is curable at room temperature or above with an appropriate curing agent. Suitable dimethylpolysiloxane rubbers are sold commercially as liquid elastomers which are mixed with a curing agent to obtain the solid rubber. Among such commercially available rubbers are those sold by Dow-Corning Corporation identified as Silastic 382 and MDX-4-4210. Such rubbers consist of two components, a first component comprising liquid uncured rubber, and a second component comprising a curing agent. The two components are mixed and the mixture is allowed to cure. Heating can be employed to enhance curing, if desired. Another suitable type of dimethylpolysiloxane rubber is a high consistency medical grade elastomer such as that sold by Dow-Corning Corporation under the designation MDF-0198. For preparing carrier compositions suitable for intrauterine or intravaginal use, the active compound, preferably in a very fine particle size, in the amount desired is throughly mixed mechanically with the uncured dimethylpolysiloxane rubber. The curing agent is then added, and the mixture is placed, e.g. by injection, in a mold having a cavity of the desired size and shape. The elastomer is allowed to cure at an appropriate temperature and time. Upon completion of the curing, the molded composition is removed at room temperature. Using the above described procedure there is obtained a dimethylpolysiloxane in which the active compound is uniformly dispersed. When in contact with body fluids in which the compound is soluble (i.e. the uterine or vaginal fluids), the compound is released into the fluids.

It will be recognized by those skilled in the art that the silicone rubber compositions useful for the purposes of this invention can also be made by other methods which are conventional in the art. One method is to form a silicone rubber composition containing the dispersed active compound, using the molding technique described above, and then to coat the composition with a very thin layer of silicone rubber. For example, a formed silicone rubber rod containing dispersed active compound can be coated with silicone rubber using conventional coating, bonding, or laminating techniques, such as by immersing the rod in a solution of uncured silicone rubber in a volatile solvent, removing the rod, evaporating the solvent, and curing the coating of silicone rubber formed thereby by heating. Alternatively, a rod containing the dispersed active compound can be fitted tightly inside a very thin hollow silicone rubber tube, and the ends can be sealed. If desired, the silicone rubber composition containing the dispersed active compound can be coated with, or enclosed tightly within, a microporous material through which the compound can pass by microporous flow, when the finished composition is bathed in vaginal or uterine fluids. The microporous material can be a microporous silicone rubber or other microporous polymer, the choice and use of which will be apparent to those skilled in the art.

Another method of making the compositions is by coating silicone rubber containing the dispersed active compound on an inert, biocompatible, insoluble, flexible core material. Preferably, the inert core is formed from silicone rubber, but other suitable conventional materials can be used.

It will also be understood that an effective amount of the active contraceptive compound can be releasably affixed to the outer surface of the silicone rubber composition, so that, when the composition is inserted into the uterus or vagina, there is an immediate release of the compound into the body fluids. The compound can be deposited or coated on the medicated silicone rubber compositions using conventional methods.

It will be apparent to those skilled in the art that, if desired, an effective amount of an X-ray contrast agent (e.g. barium sulfate) can be included in the compositions of the invention in order to render the compositions opaque to X-rays. It will also be apparent that, if desired, a non-toxic pharmaceutically acceptable filler can be added to the silicone rubber. The use of such fillers is well known in the art.

In general, the concentration of the active compound in the silicone rubber composition may vary from about 1 to about 40 percent by weight. A preferred range is from about 5 to about 20 percent. A concentration of about 10 percent has been found to be most preferred.

The rate of release of the active compound can be assessed by an in vitro test wherein the medicated carrier is placed in fresh water or fresh calcium-free Ringer's solution at 37° for successive periods of time (e.g. 24 hours), and the amount of active ingredient released after each period is assayed. For intrauterine use, a release rate equivalent to from about 1 to about 200 μg. of the active compound per day is desired. A rate from about 50 to about 150 μg. per day is preferred. For intravaginal use, a release rate of about 1 to about 5 mg. per day is desired.

It is desirable that the rate of delivery be substantially constant over the period in which the carrier composition is present in the uterine lumen or vaginal cavity. Preferably the duration of drug delivery should cover the fertile period of the female. Of course, for maximum convenience to the female, the delivery from an intrauterine composition should extend over a very long period of time, preferably one year or more, since this will avoid the inconvenience of repeated removals and reinsertions of the medicated composition. For intravaginal use, the duration of release can be about one month, and the carrier composition can be thus removed at the start of the menstrual period and re-inserted after bleeding stops. However, as long as an effective amount of the active compound can be released into the vaginal fluids, the intravaginal composition can be inserted prior to coitus and removed shortly thereafter, rather than allowing the composition to be retained in the vagina for a longer duration of time.

For administration to females, who for personal reasons do not wish to use a sustained release medicated intrauterine or intravaginal composition, an alternative method of administration of the active compound is by means of a pharmaceutically acceptable jelly, foam, cream, or suppository, which is inserted into the vagina immediately prior to coitus in a manner similar to that employed for administering conventional spermicidal compositions. [See the article entitled "Spermicides", *Population Reports;* Series H, Vol. 7, No. 5, September, 1979; published by Population Information Program, The Johns Hopkins University, Baltimore, Md.] The jelly, foam, cream, or suppository acts as a vehicle for carrying an effective amount of the active ingredient into the vaginal fluids from where it is carried into the uterus by adsorption on sperm membranes or by active transport. The active ingredient can be compounded into vaginal jellies, foams, creams, or suppositories according to procedures which are conventional in the art, by employing the usual excipients (buffers, emulsifiers, preservatives, and the like), the choice and amount of which will be apparent to those skilled in the art.

For reasons of convenience, esthetics, and more precise control of dosage, a vaginal suppository is preferred. The suppository composition must be chemically and physically stable under conditions of storage and handling, and also must be capable of melting and/or dissolving when inserted in the vagina to effect satisfactory release of the active compound into the vaginal fluids. A preferred suppository composition comprises an effective amount of the active compound in a suitable polyethylene glycol vehicle. Various polyethylene glycols, either alone or in combination, are known in the art to be useful for making vaginal suppository compositions, and the choice of a particular vehicle will be apparent to those skilled in the art.

For intravaginal use, an effective amount of the active compound can be absorbed into a biocompatible, bioinsoluble, non-toxic sponge-like soft polymer, which when inserted and retained in the vagina will release the compound by desorption into the vaginal fluids. The sponge can be allowed to remain in the vagina during coitus or it can be removed prior to coitus. Suitable polymers for this use are well known in the art, for example, a hydrophilic polymer, such as polymeric 2-hydroxyethyl methacrylate which, if desired, may contain a cross-linking agent (e.g. dimethacrylate).

The following examples illustrate the methods and compositions of the present invention.

EXAMPLE 1

Acrosin Inhibition In Vitro

The inhibition of acrosin is assessed in vitro using benzoyl arginine p-nitroanilide (BAPNA) as the enzyme substrate according to the following procedure: Acrosin (200 μl, purified from boar sperm) and a solution of the test compound (200 μl, 10 mg/ml., or 50 μl., 1 mg/ml.) in 0.05 M triethanolamine buffer, pH 7.8, are incubated at room temperature for 5 minutes. A control using the buffer solution without the test compound added is also run. A 200 μl-sample of the incubation mixture is then withdrawn and is added to a cuvette containing BAPNA (1 ml.) and triethanolamine buffer (2 ml.). The mixture is stirred and placed in a Gilford recording spectrophotometer. The increase in optical density at 383 nm is measured. One unit of acrosin activity is defined as the amount of acrosin which will cause an increase in optical density at 383 nm. of 0.001/minute. One unit of inhibitory activity is defined as the amount of inhibitor which will cause a reduction in the increase in optical density at 383 nm. of 0.001/minute.

The results of the testing of sodium alkyl sulfates for acrosin inhibition using the above described procedure are shown below in Table I.

TABLE I

| In vitro acrosin inhibition of sodium alkyl or alkenyl sulfates. | | |
|---|---|---|
| A. Sodium Salts: | | |
| Compound R of formula I | R—SO$_3$—Na Conc. of Test Solution (Mg/ml) | I Inhibition (units/mg.) |
| n-hendecyl | 10 | 0 |
| n-decyl | 10 | 0 |
| n-tridecyl | 10 | 3,200 |
| n-tetradecyl | 10 | 14,200 |
|  | 1 | 960,000 |
| n-pentadecyl | 10 | 14,300 |
| n-hexdecyl | 10 | 15,200 |
| n-heptadecyl | 10 | 18,300 |
| n-octadecyl | 10 | 26,000 |
| n-eicosyl | 10 | 31,800 |
| n-docosyl | 1 | 300,000 |
| n-tetracosyl | 1 | 123,000 |
| n-heptacosyl | 1 | 100,000 |
| 2-tetradecyl | 1 | 87,000 |
| 4-tetradecyl* | 1 | 102,000 |
| 6-tetradecyl | 1 | 90,000 |
| 7-tetradecyl | 1 | 112,000 |
| 7-hexadecyl | 1 | 123,000 |
| 8-hexadecyl | 1 | 28,000 |
| 9-octadecyl | 1 | 148,000 |
| 2-octyldodecyl | 1 | 132,000 |
| 3,7,11-trimethyldodecyl | 1 | 29,000 |
| tetrahydrogeranyl | 1 | 240,000 |
| 12-methyltridecyl | 1 | 172,000 |
| myristoleyl | 1 | 160,000 |
| myristeladyl | 1 | 216,000 |
| oleyl | 1 | 152,000 |

TABLE I-continued

| | | |
|---|---|---|
| linoleyl | 1 | 210,000 |
| 12-methyltridecane-9-yl | 1 | 152,000 |

B. Other salts:

$$R-OSO_3-M \quad \quad I$$

| Compound R of Formula I | M of Formula I | Conc. of Test Sol. (mg/ul) | Inhibition (units/mg) |
|---|---|---|---|
| $CH_3(CH_2)_{13}-$ | Ca | 10 | 48,000 |
| — | K | 10 | 62,000 |
| — | Mg | 10 | 59,000 |
| — | Li | 10 | 58,000 |
| — | $NH_4$ | 10 | 47,000 |
| — | pyridinium | 10 | 48,000 |
| $CH_3(CH_2)_{11}-$ | diethanol-ammonium | 10 | 90,000 |
| — | triethanol-ammonium | 10 | 90,000 |

*Tested as potassium salt.

EXAMPLE 2

Hyaluronidase Inhibition In Vitro

The inhibition of hyaluronidase is assessed using chondroitin sulfate as the enzyme substrate according to the following procedure:

Agar plates containing chondroitin sulfate (0.1 percent) are prepared by the following method: water solutions of 1 percent agarose, 2 M sodium chloride (0.1 vol.), 1 M sodium acetate (pH 5.0, 0.1 vol), and sodium azide (0.5 mg./ml., 0.1 vol.) are mixed and the mixture is brought to the boiling temperature. After cooling to about 65° C., a solution of chondroitin sulfate (10 mg./ml., 0.1 vol.) is added. After cooling to about 45° C., the resulting mixture (20 ml.) is poured onto a petri dish. The plates are allowed to cool to room temperature. A well 2 mm. in diameter is then cut in the agar surface. Testicular bovine hyaluronidase (Sigma Chemical Company) (5 µl., 10 mg/ml. or 1 mg/ml.) and a solution of the test compound (5 µl., 10 mg./ml.) in 1 M sodium acetate buffer, pH 5.0, are added to the well. A control using only the buffer solution without added test compound is also run. The plates are then incubated overnight (about 16 hours) at 37° C. The zones of hydrolysis of chondroitin sulfate by hyaluronidase are visualized by flooding the plate with 10 percent cetyl trimethyl ammonium bromide. The area of the zone is logarithmically proportional to the concentration of hyaluronidase. Inhibitor activity is determined by comparing the area of hydrolysis from the test compound to the area of hydrolysis from the control. The results are expressed as percent inhibition calculated as follows:

$$\text{Percent inhibition} = 100 - \frac{\text{Area of zone of inhibition for test compound}}{\text{Area of zone of inhibition for control}}$$

When tested according to the above described method the sodium alkyl sulfates of Formula I gave the following results:

TABLE II

In vitro hyaluronidase inhibition of alkyl or alkenyl sulfate salts

A. Sodium Salts:

$$R-SO_3-Na \quad \quad I$$

| Compound R of Formula I | Conc. of Test Solution (mg/ml) | % Inhibition |
|---|---|---|
| n-hendecyl | 10 | 100 |
| n-dodecyl | 10 | 71 |
| n-tridecyl | 10 | 80 |
| n-tetradecyl | 10 | 82 |
| n-pentadecyl | 10 | 60 |
| n-hexadecyl | 10 | 75 |
| n-heptadecyl | 10 | 23 |
| n-octadecyl | 10 | 30 |
| n-eicosyl | 10 | 0 |
| n-docosyl | 1 | 0 |
| n-tetracosyl | 1 | 0 |
| n-heptacosyl | 1 | 0 |
| 2-tetradecyl | 1 | 100 |
| 4-tetradecyl | 1 | 0 |
| 6-tetradecyl | 1 | 12 |
| 7-tetradecyl | 1 | 0 |
| 7-hexadecyl | 1 | 0 |
| 8-hexadecyl | 1 | 0 |
| 9-octadecyl | 1 | 7 |
| 2-octyldodecyl | 1 | 0 |
| 3,7,11-trimethyldodecyl | 1 | 39 |
| tetrahydrogeranyl | 1 | 0 |
| 12-methyltridecyl | 1 | 7 |
| myristoleyl | 1 | 13 |
| myristeladyl | 1 | 13 |
| oelyl | 1 | 0 |
| linoleyl | 1 | 0 |
| 12-methyltrideccen-9-yl | 1 | 38 |

B. Other salts:

$$R-OSO_3-M \quad \quad I$$

| Compound R of Formula I | M of Formula I | Conc. of Test Sol. (mg/ul) | % Inhibition |
|---|---|---|---|
| $CH_3(CH_2)_{13}-$ | Ca | 10 | 38 |
| — | K | 10 | 27 |
| — | Mg | 10 | 14 |
| — | Li | 10 | 27 |
| — | $NH_4$ | 10 | 14 |
| — | pyridinium | 10 | 14 |
| $CH_3(CH_2)_{11}-$ | diethanol-ammonium | 10 | 100 |
| — | triethanol-ammonium | 10 | 100 |

EXAMPLE 3

Preparation of Medicated Dimethylpolysiloxane Rubber Compositions

Method A

In a suitable container there are mixed 2430 mg. of dimethylpolysiloxane elastomer (Dow-Corning MDX-4-4210), 270 mg. of curing agent (Dow-Corning MDX-4-4210) and 300 mg. of sodium tetradecyl sulfate. After mixing, the mixture is placed in a 3 ml. syringe (no needle) and injected into a stainless steel mold block, containing two cylindrical mold cavities. The block is placed in a vacuum oven at 90° C. (slight vacuum) for about 1 hour. Upon cooling (after about 10 to 15 minutes) the molded compositions are removed to give 2 rods 3 mm. in diameter and 63 mm. in length. The content of sodium tetradecyl sulfate in each composition is 10% (W/W). Following the same procedure but using 2565 mg. of elastomer, 285 mg. of curing agent, and 150 mg. of sodium tetradecyl sulfate, there is obtained dimethylpolysiloxane compositions containing 5% of active ingredient.

Method B

Dimethylpolysiloxane elastomer (10 parts) (Dow-Corning MDX-4-4210) and curing agent (1 part) (Dow-Corning MDX-4-4210) are mixed in a suitable container, and the desired amount of sodium n-tetradecyl sulfate (to make 5, 10, or 20% W/W) is added with thorough mixing. The resulting mixture is degassed in a vacuum oven for 20-30 minutes, allowed to rest at atmospheric pressure for 10 minutes, and filled by vacuum into a glass tube of appropriate internal diameter. The depth of the filled mixture in the tube is about 10-11 inches. The tube containing the uncured rubber is allowed to stand for 10 minutes and is then heated at about 120° C. for 15 minutes to effect curing. Upon cooling, the rod of cured medicated dimethylpolysiloxane is removed from the tube by gentle pulling. For purpose of evaluation, the rod is cut into smaller pieces of a suitable length. The smaller pieces may also be formed into various shapes, such as a ring. The preparation of various rods using the above procedure is shown in Table 3, below:

TABLE 3

| Lot no. | Weight (g) | | | Rod | |
|---|---|---|---|---|---|
| | Elastomer | Curing Agent | Active Compound | % Active Compound | Diameter (m.m.) |
| 218-1 | 17.3 | 1.75 | 1.0 | 5 | 3 |
| 225-1 | 16.4 | 1.6 | 2.0 | 10 | 3 |
| 218-2 | 14.5 | 1.5 | 4.0 | 20 | 3 |
| 255-3 | 29.0 | 3.0 | 8.0 | 20 | 4 |

EXAMPLE 4

Determination of Drug Release Rate in vitro From Dimethylpolysiloxane Rubber Compositions Method A An appropriate sample of a dimethylpolysiloxane rubber compound in which is incorporated the test compound is placed in a suitable amount of calcium-free Ringers solution, and the sample and solution are incubated together at 37° C. for a period of time (e.g. 24 hours). The solution is removed and assayed for acrosin inhibition (expressed as units per milligram) using the technique described in Example 1. The equivalent amount of test compound in the removed solution is calculated from standard inhibition curves in which acrosin inhibition is plotted against concentration of the test compound. The calculated result are expressed as micrograms of test compound released per day.

The above test may be repeated for an extended period of time, for example, for 1 day to 360 days, or more, by adding fresh calcium-free Ringer's solution after each removal of the solution for assay.

Samples of a dimethylpolysiloxane rubber composition containing 10% W/W of sodium n-tetradecyl sulfate (prepared by Example 3, Method A) were tested as above described for 14 days. The sample weight was 14 mg. and the amount of added solution was 1 ml. After the 14th day, the release rate from the samples averaged 1-3 micrograms/day.

In another experiment, a dimethylpolysiloxane rubber composition weighing 400 mg. and containing 10% W/W of sodium tetradecyl sulfate (prepared by Example 3, Method A) was studied for a 90-day period. The results are shown below in Table 4.

TABLE 4

| Day | Amount of sodium n-tetradecyl sulfate released (μg/day)* |
|---|---|
| 0.08 (2 hr.) | 77 |
| 0.16 (2 hr.) | 75 |
| 0.32 (8 hr.) | 72 |
| 1 | 69 |
| 2 | 50 |
| 5 | 15 |

TABLE 4-continued

| Day | Amount of sodium n-tetradecyl sulfate released (μg/day)* |
|---|---|
| 7 | 37.5 |
| 9 | 50.0 |
| 12 | 13 |
| 13 | 0 |
| 15 | 25 |
| 18 | 28 |
| 27 | 10 |
| 42.5 | 7.6 |
| 50.5 | 10.5 |
| 57.5 | 12.0 |
| 64.5 | 8.6 |
| 72.5 | 8.3 |
| 76 | 5.6 |
| 83 | 5.1 |
| 90 | 5.0 |

*Calculated on basis of acrosin inhibition in vitro.

The mean release rate (as calculated from the data in Table 3) is 14 μg./day. The initial burst effect is believed to be caused by rapid removal of drug located on the surface of the composition. After the initial burst, the release rate levels out (after about 12 to 14 days) and thereafter remains substantially constant.

Method B

A dimethylpolysiloxane rubber rod (3 cm. long, 3 mm. diameter) weighing 341.4 mg. and containing 10% (W/W) of dispersed sodium n-tetradecyl sulfate (prepared by Example 3, Method B, lot no. 225-1) is placed in a container and is covered with 10 ml. of water. The rod and the water are incubated together at 37° C. for a seven-day period, after which the water is removed. The sodium n-tetradecyl sulfate in the water is determined by the methylene blue method as described by K. Hiyashi, *Analytical Biochemistry*, 67, 503 (1975).

The above procedure may be repeated at 7-day intervals by adding fresh water to the rod after each removal of water for assay. Table 5, below, gives the results of a test performed as above-described for 140 days.

TABLE 5

| Day | Amount of sodium n-tetradecyl sulfate released | |
|---|---|---|
| | Per 7 days (μg.) | Per day (μg.) Calc. |
| 7 | 9 | 1.3 |
| 14 | 1.9 | 0.3 |
| 21 | 34.2 | 4.9 |
| 28 | 160 | 22.8 |
| 35 | 290 | 41.4 |
| 42 | 144 | 20.6 |
| 49 | 947 | 135.3 |
| 56 | 133 | 19 |
| 63 | 111 | 16 |
| 70 | 333 | 47.5 |
| 77 | 111 | 16.0 |
| 84 | 0 | 0 |
| 91 | 105 | 15 |
| 98 | 644 | 92 |
| 105 | 1477 | 211 |
| 112 | 430 | 61.4 |
| 119 | 600 | 85.7 |
| 126 | 1500 | 214.3 |
| 133 | 2600 | 371 |
| 140 | 4000 | 571 |

Initial amount of compound in rod: 34.14 mg.
Total amount of compound released after 140 days: 12.63 mg.
Percent of compound released after 140 days: 37%

EXAMPLE 5

Antifertility Effects

A. By intrauterine administration:

Dutch belted virgin rabbits, each weighing 3-4 pounds, are randomly selected and anesthetized with sodium pentobarbital (50 µg./ml.) administered by IV drip. The uterus of each animal is exposed and a 40-mg. sample in the shape of a rod (3 mm. in diameter) of dimethylpolysiloxane rubber (as prepared in Example 3, Method A) containing 10% W/W of sodium tetradecyl sulfate is sutured into the right uterine horn at a random location in between the cervix and the uterotubal junction. The left horn is left untreated to serve as control. The rubber rod is placed into the uterine horn by passing a curved needle through it and through the uterine wall pulling the rod into the uterine lumen. The entry is closed by suturing. Animals (blank) are similarly treated using unmedicated dimethylpolysiloxane rubber to serve as a second group of controls. The animals are given 300,000 units of Duracillin ® per day (in four doses) and are allowed to recover for 14 days. Each animal is bred to a male of proven fertility and is immediately given a dose (IV) of appropoximately 100 units of human chorionic gonadotropin (HCG) to facilitate ovulation. Fourteen days after breeding, the animal are sacrificed by cervical dislocation and the uterine horns are examined for implanted embryos. The number of embryos per uterine horn are recorded.

A comparison of implanted embryos in untreated horns, in blank horns, and in treated horns is set forth below in Table 6.

TABLE 6

Inhibition of fertilization by sodium tetradecyl sulfate slowly released in the uterus

| Treatment | Number of Uterine horns | Total No. of embryos | Embryos Horn (x ± S.D.) |
|---|---|---|---|
| Untreated | 32 | 52 | 1.6 ± 0.7 |
| Blank | 13 | 14 | 1.1 ± 0.2 |
| Sodium tetradecyl sulfate* | 8 | 0 | 0 |

*Release rate from dimethylpolysiloxane, 1-3 mg./day, in vitro (Calc. on basis of acrosin inhibition).

It should be noted that in the blank animals the number of embryos per horn is smaller. This is because the sutured material decreases the available endometrial surface area for implant of the fertilized ovum. However the difference between the number of embryos in the untreated and in the blank animals is not statistically significant.

The toxicity of sodium tetradecyl sulfate, expressed as the $LD_{50}$ dose, is greater than 3.5 g/kg. orally (rats) and 342 mg./kg., (I.P.) (mice). [L. Gale et al., *J. Amer. Pharm. Assoc.*, 42, 5 (19)].

B. By intravaginal administration:

Equal volumes of K-Y-jelly ® and either Ca++ free Ringer's solution or a 10 mg./ml. solution of the compound to be tested in Ca++ free Ringer's solution are well mixed. One milliliter of this is placed into the vagina of a virgin dutch belted female rabbit using a syringe. The female is then immediately bred to a fertile buck. The female is injected I.V. with 100µ of human chorionic gonadotrophin to assure a good ovulation rate.

After approximately 14 days the females are sacrificed by cervical dislocation and the genital system examined for the number of embryos.

When tested as above described sodium tetradecyl sulfate gave the results shown below in Table 7:

TABLE 7

Inhibition of fertilization by sodium tetradecyl sulfate in female rabbits by intravaginal administration

| Treatment | No. of animals | No. of embryos | Avg. No. of Embryos per animal |
|---|---|---|---|
| control | 5 | 13 | 2.6 |
| treated | 4 | 0 | 0 |

EXAMPLE 6

Determination of Drug Release Rate and Efficacy in vivo of Medicated Dimethylpolysiloxane Rubber Compositions A. By Intrauterine Administration (a) Dimethylpolysiloxane rubber rods (3 mm. diameter shaved to 2 mm.) weighing 40 mg. each and containing 5, 10, or 20% (W/W) of sodium n-tetradecyl sulfate (prepared by Example 3, Method B, lots 218-1, 225-1, and 218-2, respectively) are inserted into the right uterine horn of virgin Dutch -belted female rabbits, as follows:

| Animal | % Sodium n-tetradecyl sulfate in rubber rod | | |
|---|---|---|---|
| | Group 1 | Group 2 | Group 3 |
| 1 | 5 | 5 | 5 |
| 2 | 5 | 5 | 5 |
| 3 | 10 | 10 | 10 |
| 4 | 10* | 10 | 10 |
| 5 | 20 | 20 | 20 |
| 6 | 20 | 20 | 20 |

*Discarded.

After 60 days the animals in Group 1 are sacrificed and the rubber rods are removed, washed, and extracted continuously with methanol for 24 hours to remove the remaining sodium n-tetradecyl sulfate. The methanol extract is evaporated. The residue is dissolved in 10% methanol-water and assayed for sodium n-tetradecyl sulfate by the methylene blue method. The amount of active compound remaining in the rod is subtracted from the amount originally present in the rod, and the difference is assumed to be the amount released during the time period. After 120 days or 60 days the animals in Group 2 and and Group 3, respectively, are sacrificed, and the rods were removed and treated as above described. The release of sodium n-tetradecyl sodium sulfate into the uterine fluids, as determined by the afore-described test procedure, after 60, 120, and 180 days is shown in Table 8, below:

TABLE 8

| % Compound in Rod | Days | Amount of sodium n-tetradecyl sulfate released (µg. per day) |
|---|---|---|
| 5 | 60 | 2.25 |
| 5 | 120 | 1.80 |
| 5 | 180 | 3.60 |
| 10 | 60 | 22.1 |
| 10 | 120 | 13.7 |
| 10 | 180 | (a) |
| 20 | 60 | 62.4 |
| 20 | 120 | 33.5 |
| 20 | 180 | (a) |

(a) Not determined because of expulsion of rod from the uterus.
(b) Five rabbits having rods containing 20% (W/W) sodium tetradecyl sulfate (as described above) sutured into both uterine horns were bred weekly for 225 days without any pregnancies noted.

B. By Intravaginal Administration

Dimethylpolysiloxane rods (4 mm. diameter) weighing 500 mg. and containing 20% (W/W) sodium n-tetradecyl sulfate (prepared by Example 3, Method B, lot no. 225-3) are formed into a circle of approximately 20 mm. diameter. The rings are inserted into the vagina of female rabbits and are held in place by sutures. The rabbits are bred either 7 or 32 days after insertion of the rings. Eleven days after breeding, the animals are sacrificed and the genital system examined for pregnancy. The rings are removed, washed, and extracted with methanol (24 hour continuous,) to remove the remaining sodium n-tetradecyl sulfate. The amount of active compound is determined by the methylene blue method, as described in Part A, above. The amount of sodium n-tetradecyl sulfate remaining in the circular rod is subtracted from the original amount present, and the difference is assumed to be the amount released over the time period. The results of the above-described test after 7-days or 32-days are shown in Table 9, below:

TABLE 9

A. After seven days:

| Animal | No. of Embryos | Amount of sodium n-tetradecyl sulfate released. (μg. per day) |
|---|---|---|
| 1 | 0 | 760 |
| 2 | 8 | 470 |
| 3 | 0 | 961 |
| 4 | 5 | 277 |
| 5 | 0 | — |
| 6 | 0 | 894 |

B. After thirty-two days:

| Animal | No. of Embryos | Amount of sodium n-tetradecyl sulfate released. (μg. per day) |
|---|---|---|
| 1 | 0 | 644 |
| 2 | 0 | — |
| 3 | 0 | 522 |
| 4 | 3 | 288 |
| 5 | 0 | — |

EXAMPLE 7

Removal of cumulus oophorus from ova, in vitro

Female rabbits are given 100 units of pregnant mares serum (PMS), IM, and 134 units of HCG, IV. After 13 hours the animals are sacrificed, and the ovaries are excised. The ovaries are submerged in calcium-free Ringer's solution containing 20% rabbit serum which had been heated to 55° C. for 20 minutes. Ova with cumulus intact are removed and placed in calcium-free Ringer's solution for incubation at 37° C. Hyaluronidase (10 μl.) of a 10 mg./ml. solution in calcium-free Ringer's solution is added to 20 ova in 1 ml. of the incubation medium. To 10 ova in the same medium is added 10 μl. of a solution of sodium n-tetradecyl sulfate (10 mg./ml.) in calcium-free Ringer's solution. To 10 other ova in the same media is added 10 μl. of calcium-free Ringer's solution as control. The mixtures are incubated at 37° C., and the cumulus oophorus is examined at 15 minute intervals with an American Optical stereomicroscope. In the absence of sodium tetradecyl sulfate, the cumulus oophorus is completely removed. With sodium n-tetradecyl sulfate the cumulus remains substantially intact.

EXAMPLE 8

Removal of Zona Pellucida from ova, in vitro

Female rabbits are given 100 units of pregnant mares serum (PMS), IM, and 134 units of HCG, IV. After 13 hours the animals are sacrificed and the ovaries are excised. The ovaries are submerged in calcium-free Ringer's solution. Ova are removed and placed in 1 ml. of calcium-free Ringer's solution The solutions are all shaken vigorously for 5 to 10 minutes, which rids the ova of the cumulus oophorus and the corona radiata. Acrosin (isolated from boar sperm) (100 μl., of a solution containing 2000 U/ml. in 0.1 M sodium acetate and 0.02 M calcium chloride) is added to each of 10 ova. To each of 10 other ova in the same medium is added 10 μl. of solution of sodium n-tetradecyl sulfate (10 mg./ml.) in calcium-free Ringer's solution. To 10 other ova is added 10 ml. of calcium-free Ringer's solution as a control. The solutions are all incubated at 37° C. The zona pellucida is observed at 15 minute intervals with an American Optical stereomicroscope. In the absence of sodium n-tetradecyl sulfate, the zona pellucida is completely removed. With sodium n-tetradecyl sulfate present, the zona pellucida remains substantially intact.

EXAMPLE 9

Preparation of Coated Medicated Dimethylpolysiloxane Rubber Compositions

Dimethylpolysiloxane rubber rods (3 mm. diameter) containing 25% (W/W) sodium n-tetradecyl sulfate are prepared by the procedure described in Example 3, Method B. The rods are cut into one-inch pieces. A coating solution is prepared by dissolving 12.5 grams of dimethylpolysiloxane elastomer (DOW-Corning MDX-4-4210) in 37.5 ml of methylene chloride and then dissolving 1.88 grams of curing agent (Dow-Corning MDX-4-4210) therein. A straight pin is placed in the end of each one inch piece of rod. The piece of rod, held by the pin, is dipped into the above solution, and the rod is withdrawn from the solution and drained. The piece of rod is rotated as methylene chloride evaporates. The coated rods are placed in an oven at 120° C. for 10 minutes to cure the coating. The coated rods are then placed in a vacuum oven at 40° C. overnight to remove all methylene chloride. A second and third coat can be applied by the above method.

The release of sodium n-tetradecyl sulfate from the coated medicated rods, prepared as above-described, into water is shown in Table 10, below:

TABLE 10

| Days | Amount of sodium n-tetradecyl sulfate released.[a] (mg. per 7 days) | | |
|---|---|---|---|
| | 1 coat | 2 coat | 3 coat |
| 7 | 0 | 0 | 0 |
| 14 | 0.14 | 0 | .02 |
| 21 | 77.4 | .03 | 0 |
| 28 | 414.0 | 628.0 | 10.0 |
| 35 | 128.0 | 124.0 | 142.0 |
| 42 | 586.0 | 96.0 | 0 |
| 49 | 370.0 | 186.0 | 186.0 |
| 56 | 524.0 | 135.0 | 143.0 |
| 63 | 571.0 | 183.0 | 194.0 |
| 70 | 524.0 | 174.0 | 174.0 |
| 77 | 471.0 | 229.0 | 157.0 |
| 84 | 386.0 | 170.0 | 160.0 |
| 91 | 330.0 | 200.0 | 140.0 |
| 98 | 349.0 | 190.0 | 159.0 |
| 105 | 240.0 | 224.0 | 196.0 |
| 112 | 329.0 | 121.0 | 157.0 |
| 119 | 286.0 | 100.0 | 150.0 |
| 126 | 430.0 | 92.0 | 156.0 |

[a]Weight of rods: 500 mg.; amount of water added: 10 ml.; temperature: 37° C.; active compound determined by methylene blue method.

EXAMPLE 10

Efficacy of a Vaginal Suppository in Female Rabbits

Suppositories weighing 100 mg. are made to contain 1 mg. of sodium n-tetradecyl sulfate in a vehicle consisting of 35% polyethylene glycol 400, 35% polyethylene glycol 1540, and 30% polyethylene glycol 4000. A suppository is placed in the vagina of each of six female Dutch belted rabbits. After 15 minutes, each rabbit is bred to a buck of proven fertility and is injected with 100 I.U. of human chorionic gonadotropin. Each of six control animals are similarly treated using identical 100 mg. suppositories made from the same vehicle without the active compound. The animals are sacrificed after 12 days and are examined for embryos. The results are shown below:

| Treatment | No. of Animals | Total No. of Embryos | Embryos Per Animal ($\bar{x}$ + std. dev.) |
|---|---|---|---|
| sodium n-tetradecyl sulfate | 6 | 3 | $0.5 \pm 1.2$ |
| control | 6 | 23 | $3.83 \pm 3.6$ |

What is claimed is:

1. A contraceptive composition suitable for insertion and comfortable retention in the uterine lumen which comprises: (a) about 1 to about 40 percent by weight of a compound of the formula:

$$R-OSO_3-M$$

wherein R is:
 (a) $C_{11}$–$C_{30}$ straight chain alkyl or alkenyl;
 (b) $C_{10}$–$C_{30}$ branched chain alkyl or alkenyl, the α-carbon of which is not branched; or
 (c) $C_{13}$–$C_{30}$ branched chain alkyl or alkenyl, the α-carbon of which is branched;
and M is a pharmaceutically acceptable non-toxic cation; and (b) about 60 to about 99 percent by weight of a biocompatible, bioinsoluble, flexible silicone rubber carrier matrix, said matrix being capable of continuously releasing said compound into the uterine fluids at a controlled rate over a prolonged period of time.

2. A composition as defined in claim 1 wherein the silicone rubber is dimethylpolysiloxane.

3. A composition as defined in claim 1 or 2, wherein R is $C_{11}$–$C_{20}$ straight chain alkyl.

4. A composition as defined in claim 3 wherein M is sodium.

5. A composition as defined in claim 3 wherein R is n-tetradecyl.

6. A composition as defined in claim 5 wherein M is sodium.

7. A composition as defined in claim 1 or 2 wherein R is 2-tetradecyl, 4-tetradecyl, 6-tetradecyl, 7-tetradecyl, 7-hexadecyl, 8-hexadecyl, 9-octadecyl, 12-methyltridecyl, tetrahydrogeranyl, 3, 7, 11-trimethyldodecyl, 2-octyldecyl, myristoleyl, myristeladyl, oleyl, eladyl, linoleyl, or 13-methyltridec-9-enyl.

8. A composition as defined in claim 7 wherein M is sodium.

* * * * *